United States Patent [19]
Björk et al.

[11] Patent Number: 5,434,156
[45] Date of Patent: Jul. 18, 1995

[54] USE OF DIPHENYLBUTYL-PIPERAZINECARBOXAMIDES IN THE TREATMENT OF SUBSTANCE DISORDERS

[75] Inventors: Anders Björk, Bjärred; Erik Christensson, Lund, both of Sweden

[73] Assignee: Pharmacia AB, Sweden

[21] Appl. No.: 949,869

[22] PCT Filed: Mar. 23, 1992

[86] PCT. No.: PCT/SE92/00182
§ 371 Date: Oct. 12, 1993
§ 102(e) Date: Oct. 12, 1993

[87] PCT Pub. No.: WO92/16211
PCT Pub. Date: Oct. 1, 1992

[30] Foreign Application Priority Data

Mar. 22, 1991 [SE] Sweden .................... 9100860

[51] Int. Cl.6 ............................................. A61K 31/495
[52] U.S. Cl. ........................................ 514/255; 514/811
[58] Field of Search ............... 514/255, 810, 811, 812, 514/813

[56] References Cited
U.S. PATENT DOCUMENTS 4,308,387 12/1981 Björk et al. .................. 514/255
4,385,057 5/1983 Björk et al. .................. 514/255
4,447,433 5/1984 Björk et al. .................. 514/255

OTHER PUBLICATIONS

Life Sciences, vol. 47, 1990, Eva Eriksson: "Amperozide, a putative anti-psychotic drug: uptake inhibition and release of dopamine in vitro in the rat brain" pp. 2111–2117, see especially p. 2116.

Pharmacology & Toxicology Supplement, vol. 1, 1990, J. Svartengren et al: "Receptor binding properties of amperozide," pp. 8–11.

Primary Examiner—Raymond Henley, III
Attorney, Agent, or Firm—Pravel, Hewitt, Kimball & Krieger

[57] ABSTRACT

The present invention relates to the relief or prevention of withdrawal syndrome resulting from addiction to alcohol and/or the suppression of dependence on alcohol by administering to a person in need thereof, an effective amount certain diphenylbutyl-piperazine-carboxamides including 4-[4,4-bis(4-fluorophenyl)butyl]-N-ethyl-1-piperazine-carboxamide which is also known as amperozide.

4 Claims, No Drawings

USE OF DIPHENYLBUTYL-PIPERAZINECARBOXAMIDES IN THE TREATMENT OF SUBSTANCE DISORDERS

FIELD OF THE INVENTION

The present invention relates to a new use of certain diphenylbutyl-piperazinecarboxamides, especially amperozide, 4-[4,4-bis(4-fluorophenyl)butyl]-N-ethyl-1-piperazinecarboxamide, and salts thereof, in the treatment of substance abuse disorders. More particularly, this invention relates to the amelioration of withdrawal symptoms and to modifying drug-seeking behaviour.

BACKGROUND OF THE INVENTION

Different classes of neuronal receptors and neurotransmitters in the brain have been implicated in the complex mechanisms underlying the compulsive drinking of alcohol. Experimental findings have favoured the opioid, dopaminergic, serotonergic, and benzodiazepine receptor subtypes. Whether the receptor category is pre- or postsynaptic in nature and whether neurotransmitter synthesis and/or release is equally involved in the manifestation of alcohol drinking is presently unknown.

Drug dependency is extremely difficult to escape. This is true whether the dependency is one based on ethanol, amphetamine, barbiturates, benzodiazepines, cocaine, nicotine, opioids, and phencyclidine or the like. Despite active research, there are as yet no drugs that specifically can antagonize for example the alcohol craving in alcohol-dependent subjects. Previous research demonstrated that for example serotonin uptake blockers (e.g. zimelidine, sertraline) reduce voluntary alcohol consumption in rats and humans. However, the mechanism of action of these compounds is not Well understood. There is considerable experimental evidence that the effects on alcohol intake may be an expression of a more general inhibiting role that serotonin plays in consummatory behaviour. Indeed serotonin uptake blockers and serotonin agonists have been shown to reduce a number of oral consummatory behaviours such as the intake of food as well as a variety of flavoured fluids such as alcohol.

The serotonin uptake blocker, sertraline, has been found to reduce alcohol intake in rats. Concurrent with the effect on alcohol drinking, however, sertraline lowered the intake of food and water and caused an overall decline in body weights (Gill K. et al., Alcohol 5:355–358, 1988; Myers R. D. and Quarfordt S. D., Pharmacol. Biochem. Behav. 40:923-28, 1991). Clearly, it is likely that the action of sertraline on alcohol intake is related to a serotonin uptake blocker's effect on oral consummatory behaviour. Hence, a decline also in the drinking of alcohol would not be unexpected. Furthermore, during the period following the sertraline treatment, the intake of alcohol rose toward the pretreatment level. There is accordingly a need for a more specific and effective agent to be used for treating abuse disorders.

SUMMARY OF THE INVENTION

It has now unexpectedly been found that diphenylbutyl-piperazinecarboxamides of the formula

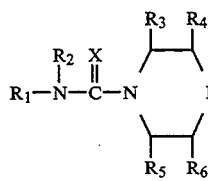

wherein $R_1$ and $R_2$ are groups independently selected from the group of H, alkyl chains, straight or branched, with 1–10 carbon atoms, cycloalkyl with 3–8 carbon atoms, aralkyl with 7–9 carbon atoms, alkenyl with 2–10 carbon atoms, phenyl unsubstituted or substituted by one to three groups selected from halogen, especially F, Cl and Br, lower alkyl with 1–5 carbon atoms, lower alkoxy with with 1–5 carbon atoms, amine unsubstituted or substituted by one or two lower alkyl groups with 1–5 carbon atoms, —$CF_3$ and —CN groups, $R_3$, $R_4$, $R_5$ and $R_6$ are groups independently selected from H, lower alkyl having from 1–3 carbon atoms and phenyl, $R_7$ is selected from hydrogen, halogen especially F, Cl and Br, lower alkoxy with 1–3 carbon atoms and —$CF_3$, and X is O or S and pharmaceutically acceptable salts thereof, are extremely effective and specific in suppression of alcohol dependence.

This finding opens up a completely new method of treating dependence on drugs, alcohol, nicotine and the like. The actual substances have been found to be both chemically and pharmacologically different from those drugs suggested hitherto for the treatment of drug dependence.

Specifically the invention relates to the relief or prevention of a withdrawal syndrome resulting from addiction to a drug or substance of abuse and/or for the suppression of dependence on drugs or substances of abuse.

The substances as such are known from the prior art (see U.S. Pat. No. 4,308,387, which is hereby incorporated by reference) as well as their use use in other areas of medicine (see U.S. Pat. Nos. 4,447,433, 4,385,057 and 5,013,735).

DETAILED DESCRIPTION OF THE INVENTION

The present invention relates to a method for treating substance abuse disorders by administering to a patient suffering from abuse a therapeutically effective amount of a diphenylbutyl-piperazinecarboxamide according to Formula I, as defined above. The at present preferred substances are those wherein $R_1$ is methyl, ethyl or n-, iso- or cyclopropyl, $R_2$ is H, $R_3$, $R_4$, $R_5$ and $R_6$ are hydrogen or $R_3$ and $R_6$ are hydrogen and $R_4$ and $R_5$ are methyl, or $R_4$ and $R_5$ are hydrogen and $R_3$ and $R_6$ are methyl, $R_7$ is hydrogen or halogen, preferrably one substituent on each benzene ring being F, and X is O, or physiologically acceptable salts thereof.

The most preferred substance at present is amperozide or a physiologically acceptable salt thereof. Amperozide, with the chemical name 4-[4,4-bis(4-fluorophenyl)butyl]-N-ethyl-1-piperazinecarboxamide, is a psychotropic compound developed by Björk A.K.K. et al (U.S. Pat. No. 4,308,387) with effects preferentially on emotional behaviour mediated by an action on the limbic brain areas (Christensson E. and Björk A., Pharmacol. Toxicol. 66: Suppl. I, 5–7, 1990). While the mechanism by which amperozide affects emotional behaviour remains unknown, research indicates that amperozide is a serotonergic antagonist (Svartengren J. and Simonsson P., Pharmacol. Toxicol. 66: Suppl. I, 8–11, 1990) and, furthermore, acts as a serotonin uptake blocker (Eriksson E., Life Sci. 47:2111–2117, 1990). Recent findings suggest that amperozide modifies also the glutaminergic neurotransmission that would be of importance for learning and memory.

In said article by Eriksson E., a statement is cited telling that "serotonin uptake inhibitors might be useful in the treatment of abuse, e.g. citalopram and zimelidine, which appear to suppress the abuse fo alcohol". However, there is in said article no mention of the fact that serotonin uptake blockers have been shown to reduce a number of oral consummatory behaviours. Apparently, a serotonin uptake blockade does not in itself constitute the basis for a pharmacological specificity of action in the treatment of substance abuse disorders. Hence, the general statement in said article by Eriksson E. does not give a man of ordinary skill in the art the basis for selecting substances which meet the need for more specific and effective agents to be used in the treatment of substance abuse disorders.

The invention is also related to the use of a therapeutically effective amount of a substance according to Formula 1 for preparation of a composition for the treatment of substance abuse disorders, as well as to the composition as such.

Repeated administration to a subject of certain drugs such as opiates, (e.g. morphine), cocaine, benzodiazepines (e.g. diazepam), or substances of abuse such as alcohol or nicotine can lead to physical and/or psychological dependence upon that drug or substance. When the drug or substance of abuse is withdrawn from a dependent subject, the subject develops certain symptoms including sleep and mood disturbance and intense craving for the drug or substance of abuse. These symptoms may be collectively described as a withdrawal or abstinence syndrome in connection with the present invention.

Formulations comprising the pharmacologically active compounds of this invention are disclosed in U.S. Pat. Nos. 4,308,387, 4,385,057, and 5,013,735 which are hereby incorporated by reference. As examples of such formulations, expected to be suitable for use for treatment of substance abuse disorders, can be mentioned:

Capsules containing (per capsule):

| active ingredient | 10 mg |
| lactose | 250 mg |
| starch | 120 mg |
| magnesium stearate | 5 mg |

Tablets containing (per tablet):

| active ingredient | 10 mg |
| avicel | 108 mg |
| colloidal silica | 10 mg |
| talc | 20 mg |

-continued

| magnesium stearate | 2 mg |

Injection solution (per 100 ml):

| active ingredient | 1000 mg |
| metagin | 100 mg |
| NaCl | 700 mg |
| HCl 0.1N to pH 3.5 | |
| Aq. sterilisata ad | 100 ml |

A therapeutically effective amount, expressed in mg per day, of the substance defined above, for instance amperozide, for use in the treatment of substance abuse disorders, would be from about 0.1 to about 40 mg, preferably 0.1 to 20 mg, and especially 1–20 mg, depending on the specific condition to be treated, the age and weight of the specific patient and the specific patient's response to the medication. The exact individual dosage, as well as the daily dosage, will accordingly be determined according to standard medical principles under the direction of a physician. The animal tests referred to below have indicated that administration twice a day gives a therapeutical effect, and this would be expected to be the case also when the substance is administered to a human being.

The active ingredient may accordingly be expected to be administered to a patient in need of such treatment according to usual routes of administration and in usual forms. These include solutions, suspensions, emulsions, tablets, capsules, and powders prepared in pharmaceutically acceptable carriers for oral administration or sterile solution for parenteral administration.

In one embodiment of the invention the daily dose of the active substance is administered continuosly at a substantially constant level, over a given time period, for instance by an injection port or pump.

Various additives to enhance the stability or ease of administration of the drug are contemplated. The pharmaceutical composition may also contain additional therapeutically useful substances other than the pharmacologically active compounds of this invention for combination treatment.

Twenty years of research has consistently demonstrated that drugs that are abused by man are usually self-administered by laboratory animals. Ethanol, amphetamine, barbiturates, benzodiazepines, cocaine, nicotine opioids, and phencyclidine and the like are just a few examples of substances abused by man and self-administered in animal models. The value of animal models for investigating the pharmacological and behavioural mechanisms underlying drug dependence has been repeatedly demonstrated. In fact, the animal models are our only recourse for the investigation of compounds to ameliorate or modify drug-seeking behaviour. In relation to this there is considerable experimental evidence supporting that a commonalty in the mechanism of the addictive process itself exists in the brain stem which underlies the predilection to abuse the above mentioned drugs.

The following examples are intended to illustrate the present invention without in any way limiting the scope thereof:

EXAMPLE 1

Preparation of an Amperozide Tablet

Amperozide tablets were prepared having the following composition:

| | |
|---|---|
| Amperozide hydrochloride | 5.0 mg |
| Lactose | 105.5 mg |
| Microcrystalline cellulose | 13.0 mg |
| Sodium Starch Glycolate | 5.2 mg |
| Silicone Dioxide | 0.65 mg |
| Magnesium Stearate | 0.65 mg |

The core composition was coated with a conventional sucrose coating to give a tablet for oral use.

EXAMPLE 2

The Effect of Amperozide on Cyanamide-induced Alcohol Drinking in Rats

The effect of amperozide administered systemically was determined in Spraque-Dawley rats induced to drink alcohol chronically by a series of intraperitoneal injections of cyanamide according to experimental procedures described previously (Critcher E. C. and Myers R. D., Alcohol 4:347–353, 1987). Intake of food and water and measures of body weight gain were recorded.

Amperozide given subcutaneously in a dose of 2.5 mg/kg b.i.d. over a three-day interval markedly altered the volitional consumption of alcohol. An immediate effect occurred following the administration of amperozide in terms of both absolute amount in g/kg and proportion of alcohol to water. The mean g/kg intake was reduced (P less than 0.01) by about 60% from the pretest level 4.4 g/kg to 1.6 g/kg of alcohol. The proportion of alcohol to total fluid consumed was similarly reduced from the pretest level. Of special importance is the fact that there were no significant effects produced by amperozide in terms of a change in the body weight or in the amounts of food and water consumed by the rats during the treatment period in comparison with the pretest level, demonstrating a pharmacological specificity of action of this drug.

Particularly notable is the finding that amperozide administered in a steady state dose regimen by an Alzet osmotic minipump implanted in the intrascapular space in a dose of 5 mg/kg/day for seven days attenuated significantly alcohol drinking in the cyanamide-treated rat in terms of both absolute g/kg and proportion of alcohol to water. In respect of the absolute intake of alcohol, the mean g/kg ingested decreased (P less than 0.01) from 7.0 g/kg to 3.4 g/kg of alcohol during the delivery of amperozide. In the four-day period following the systemically administered amperozide, i.e. after the minipump was depleted of the drug, the absolute g/kg intake of the rats was still suppressed. Moreover when the preference pattern was retested at 30, 70, 110 and 140 day intervals following the cessation of amperozide delivery the decline persisted. Concurrent with the effect on alcohol drinking, the consumption of food as well as level of body weight was unaffected by amperozide. These results with amperozide provide the first demonstration of an enduring action of any drug on aberrant alcohol drinking and clearly demonstrate that the actual compounds are useful for preventing or reducing dependency on dependency-inducing agents.

We claim:

1. A method for the relief or prevention of a withdrawal syndrome resulting from addiction to alcohol and/or for the suppression of dependence on alcohol which comprises administering an effective amount of a diphenylbutyl-piperazinecarboxamide of the formula

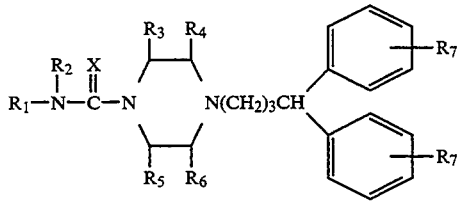

wherein $R_1$ and $R_2$ are groups independently selected from the group of H, alkyl chains, straight or branched, with 1–10 carbon atoms, cycloalkyl with 3–8 carbon atoms, aralkyl with 7–9 carbon atoms, alkenyl with 2–10 carbon atoms, phenyl unsubstituted or substituted by one to three groups selected from halogen, lower alkyl with 1–5 carbon atoms, lower alkoxy with with 1–5 carbon atoms, amine unsubstituted or substituted by one or two lower alkyl groups with 1–5 carbon atoms, —$CF_3$ and —CN groups, $R_3$, $R_4$, $R_5$ and $R_6$ are groups independently selected from H, lower alkyl having from 1–3 carbon atoms and phenyl, $R_7$ is selected from hydrogen, halogen lower alkoxy with 1–3 carbon atoms and —$CF_3$, and X is O or S, or a physiologically acceptable salt thereof.

2. A method according to claim 1 wherein $R_1$ is methyl, ethyl or n-, iso- or cyclopropyl, $R_2$ is H, $R_3$, $R_4$, $R_5$ and $R_6$ are hydrogen or $R_3$ and $R_6$ are hydrogen and $R_4$ and $R_5$ are methyl, or $R_4$ and $R_5$ are hydrogen and $R_3$ and $R_6$ are methyl, $R_7$ is hydrogen or halogen, and X is O.

3. A method according to claim 2, wherein the diphenylbutylpiperazinecarboxamide is 4-[4,4-bis(4-fluorophenyl)butyl]-N-ethyl-1-piperazinecarboxamide or a physiologically acceptable salt thereof.

4. A method according to claim 3, wherein the diphenylbutylpiperazinecarboxamide is administered in a daily dose of from 0.1 to 40 mg.

* * * * *